United States Patent
Cho et al.

(10) Patent No.: US 7,623,917 B2
(45) Date of Patent: Nov. 24, 2009

(54) METHOD OF OPTIMIZING DATA COLLECTION AND THERAPY DELIVERY BASED ON RESPIRATION

(75) Inventors: Yong K. Cho, Maple Grove, MN (US); John E. Burnes, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 581 days.

(21) Appl. No.: 11/322,761

(22) Filed: Dec. 30, 2005

(65) Prior Publication Data

US 2007/0156193 A1 Jul. 5, 2007

(51) Int. Cl.
  *A61N 1/36* (2006.01)
(52) U.S. Cl. ............... 607/20; 607/17; 600/529
(58) Field of Classification Search ......... 607/18
  See application file for complete search history.

(56) References Cited

U.S. PATENT DOCUMENTS

| | | | |
|---|---|---|---|
| 5,480,441 A | | 1/1996 | Hudrlik |
| 5,540,727 A | * | 7/1996 | Tockman et al. ............ 607/18 |
| 5,836,976 A | * | 11/1998 | Min et al. .................. 607/6 |
| 5,954,752 A | | 9/1999 | Mongeon et al. |
| 5,964,788 A | | 10/1999 | Greenhut |
| 6,141,590 A | * | 10/2000 | Renirie et al. ............. 607/20 |
| 6,626,839 B2 | | 9/2003 | Doten et al. |
| 6,876,881 B2 | | 4/2005 | Baumann et al. |
| 2003/0153953 A1 | * | 8/2003 | Park et al. ............... 607/17 |
| 2003/0204212 A1 | * | 10/2003 | Burnes et al. ............. 607/17 |
| 2004/0034391 A1 | * | 2/2004 | Baumann et al. .......... 607/25 |
| 2004/0199210 A1 | * | 10/2004 | Shelchuk ................. 607/17 |
| 2005/0109338 A1 | | 5/2005 | Stahmann et al. |
| 2006/0020294 A1 | * | 1/2006 | Brockway et al. ........ 607/17 |

FOREIGN PATENT DOCUMENTS

| | | |
|---|---|---|
| EP | 1410756 A | 4/2004 |
| EP | 1486232 A | 12/2004 |
| WO | WO20050122902 A | 12/2005 |
| WO | WO20050123178 A | 12/2005 |

OTHER PUBLICATIONS

International Search Report, PCT/US2006/062070, Apr. 25, 2007, 6 pages.

* cited by examiner

*Primary Examiner*—Carl H. Layno
*Assistant Examiner*—Jon-Eric C. Morales
(74) *Attorney, Agent, or Firm*—Michael C. Soldner

(57) ABSTRACT

A method and system for improving or optimizing the collection of data from and the delivery of therapy to a patient by an implantable medical device (IMD) is disclosed which uses information about the patient's respiratory cycle.

26 Claims, 9 Drawing Sheets

US 7,623,917 B2

METHOD OF OPTIMIZING DATA COLLECTION AND THERAPY DELIVERY BASED ON RESPIRATION

FIELD

The present invention relates generally to medical devices, and more particularly to implantable medical devices (IMDs).

BACKGROUND

Cardiac function varies during respiration, a phenomenon referred to as the "respiration effect." Pressures in the right atrium and thoracic vena cava depend on intrapleural pressure ($P_{pl}$). During inspiration, the chest wall expands and the diaphragm lowers. This causes a fall in $P_{pl}$ that leads to expansion of the lungs and cardiac chambers (e.g., right atrium and right ventricle), and a reduction in right atrial and ventricular pressures. As right atrial pressure falls during inspiration, the pressure gradient for venous return to the right ventricle increases. During expiration, the opposite occurs. Thus, the net effect of respiration is that increasing the rate and depth of ventilation facilitates venous return and ventricular stroke volume.

The respiration effect is typically seen earlier in the right ventricle than in the left ventricle, since inspiration and expiration tend to affect the hemodynamics of the right ventricle more directly than that of the left ventricle. The effect of respiration on the right side of the heart is subsequently observed on the left side of the heart, typically after a delay of about one cardiac cycle or more, as changes in the mechanical function of the right side of the heart are observed on the left side of the heart in the next few cardiac cycles. This time lag may become more pronounced in certain patients as cardiopulmonary functions deteriorate (for example without limitation, due to the progression of heart failure, pulmonary edema, and pulmonary hypertension).

To date, various methods have been proposed for detecting respiration with an implantable medical device (IMD). For example, minute ventilation sensors have been used to measure respiration by monitoring cyclic changes in transthoracic impedance that occur during respiration. Intracardiac electrogram (EGM) amplitude modulation has also been used to monitor respiration. A technique for monitoring respiration that uses blood pressure signals has also been proposed.

The respiration effect may cause fluctuations in a number of hemodynamic parameters that may be the subject of monitoring and/or the basis for therapy decisions. Such fluctuations may affect the ability of a physician (or an IMD) to interpret the monitored hemodynamic parameters and/or to provide (or deliver) appropriate therapy.

SUMMARY OF THE INVENTION

In certain embodiments of the invention, a method of collecting hemodynamic data from a patient includes monitoring the respiratory cycles of a patient, and identifying a timing reference point in the respiratory cycle from which to base the timing of the collection of hemodynamic data.

In certain other embodiments of the invention, a method of optimizing therapy delivery includes monitoring the respiratory cycles of a patient, and varying therapy parameters according to the phase of the respiratory cycle.

In another embodiment of the invention, a medical device system for improving data collection and/or therapy delivery is disclosed which monitors the respiratory cycles of a patient to optimize the timing of data collection and/or therapy delivery.

DETAILED DESCRIPTION

Figure 1:
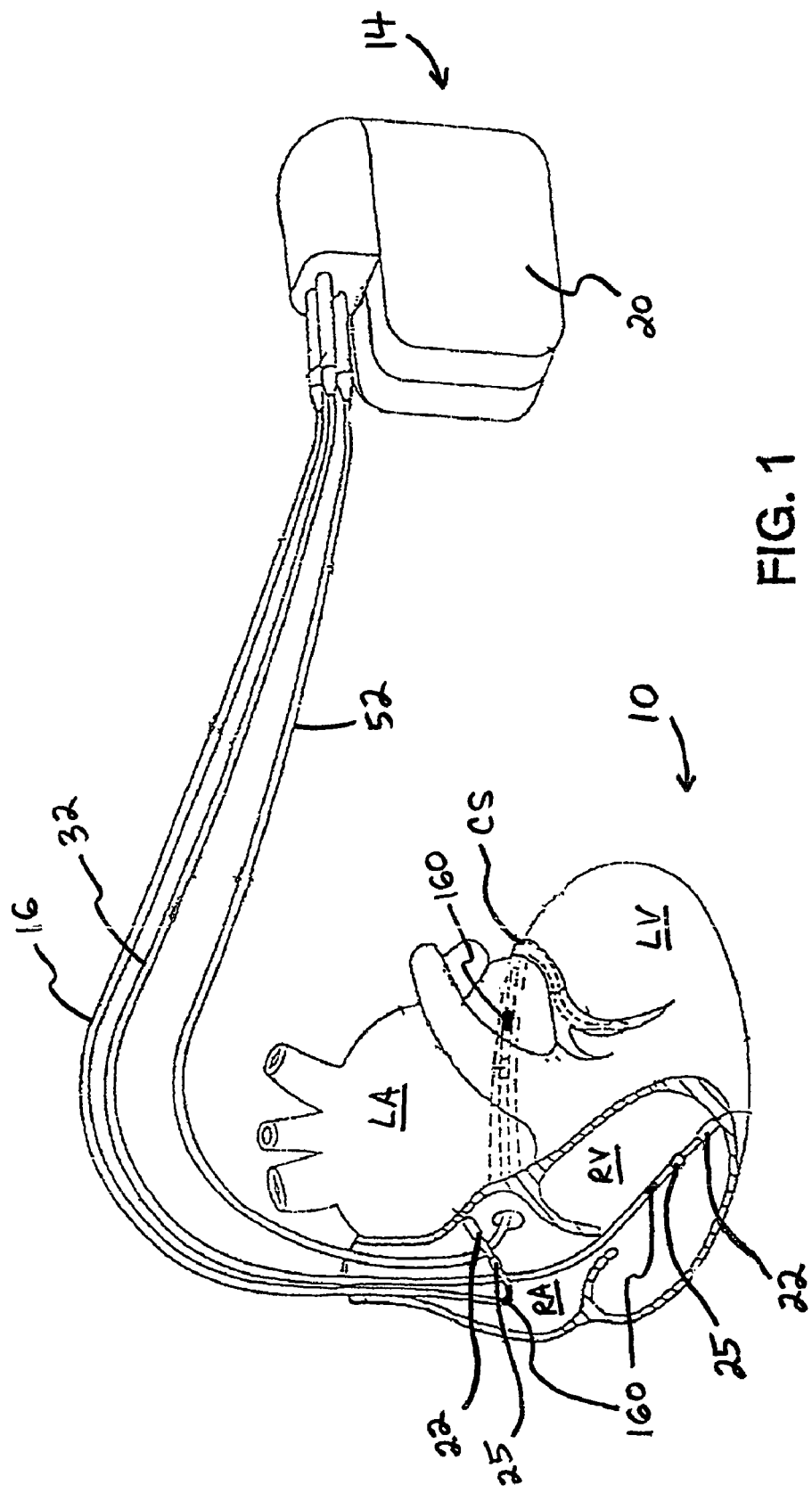
FIG. 1 is a schematic diagram depicting a multi-channel, atrial and bi-ventricular, monitoring/pacing IMD in which embodiments of the invention may be implemented.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

The heart and lungs are functionally linked for oxygen and carbon dioxide transport. In addition, the heart and lungs are mechanically linked through their close proximity within the equi-pressure intrathoracic cavity, neurally linked through reflex pathways, and humorally linked through endocrine and metabolic function. These functional, mechanical, neural and humoral linkages simultaneously operate to create a complex system. In monitoring cardiac function and delivering therapy using implantable medical devices (IMDs), these linkages are often not taken into account.

The "respiration effect" is an example of the result of such linkages. The effects of respiration on hemodynamic parameters tend to be exhibited in the right ventricle before the left ventricle. For example, there is typically a difference of one or more cardiac cycles in the occurrence of a given respiration effect between the right and left ventricles. This difference may become more pronounced as cardiac function deteriorates, for example, in a heart failure patient. Methods and systems in accordance with certain embodiments of the invention may therefore include monitoring of the respiratory cycle (inspiration and expiration) to improve data collection and/or to optimize therapy delivery. Certain embodiments of the invention may include, or may be adapted for use in, diagnostic monitoring equipment, external medical device systems, and implantable medical devices (IMDs), including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

FIG. 1 is a schematic representation of an implantable medical device (IMD) 14 that may be used in accordance with certain embodiments of the invention. The IMD 14 may be any device that is capable of measuring hemodynamic parameters (e.g., blood pressure signals) from within a ventricle of a patient's heart, and which may further be capable of measuring other signals, such as the patient's electrogram (EGM).

In FIG. 1, heart 10 includes the right atrium (RA), left atrium (LA), right ventricle (RV), left ventricle (LV), and the coronary sinus (CS), an opening in the right atrium that couples the RA to the great vein.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

It should be noted that the IMD 14 may also be an implantable cardioverter defibrillator (ICD), a cardiac resynchronization therapy (CRT) device, an implantable hemodynamic monitor (IHM), or any other such device or combination of devices, according to various embodiments of the invention.

Typically, in pacing systems of the type illustrated in FIG. 1, the electrodes designated above as "pace/sense" electrodes are used for both pacing and sensing functions. In accordance with one aspect of the present invention, these "pace/sense" electrodes can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors for measuring systolic and diastolic pressures, and a series of spaced apart impedance sensing leads for deriving volumetric measurements of the expansion and contraction of the RA, LA, RV and LV.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
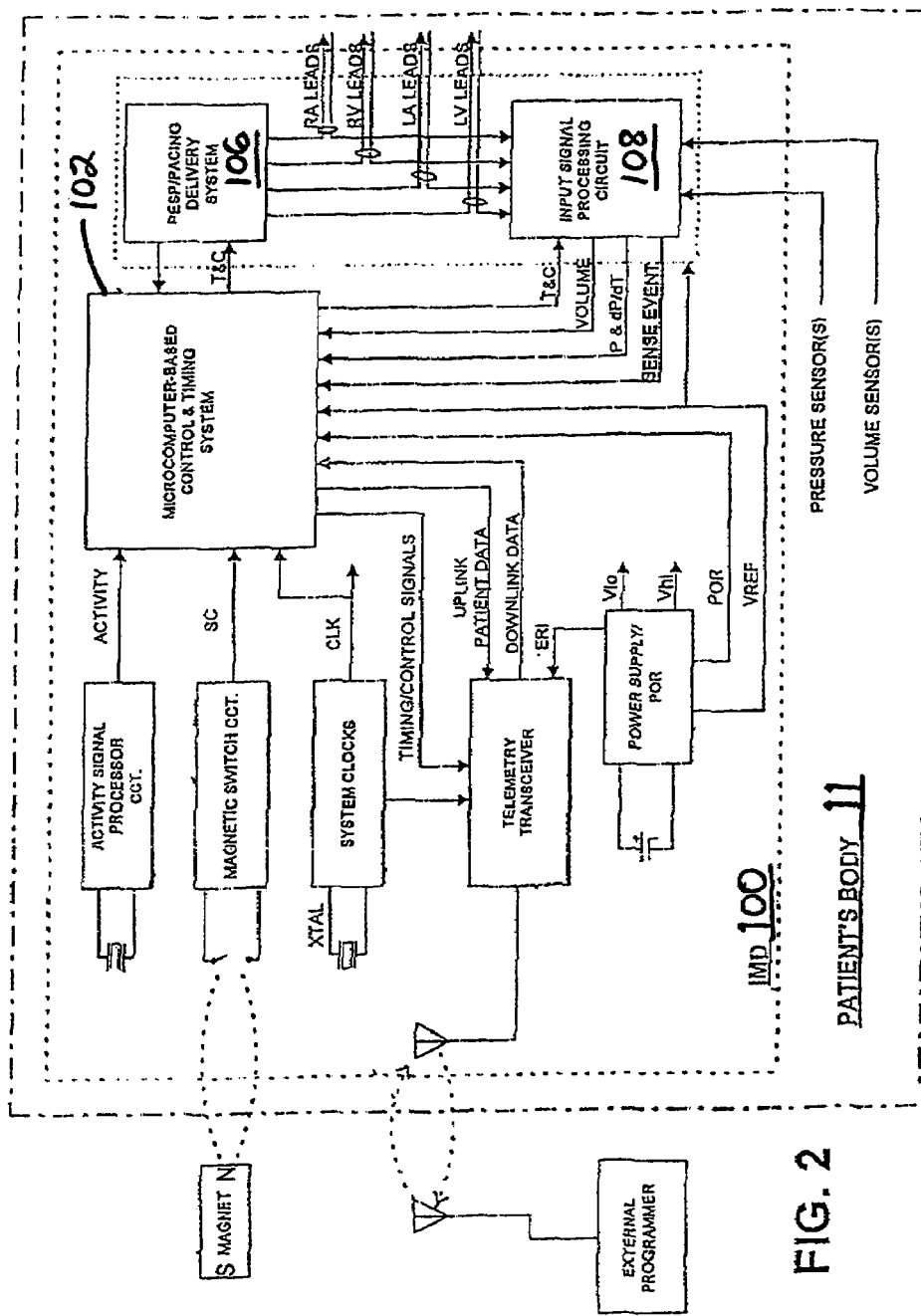
FIG. 2 is a simplified block diagram of an embodiment of IMD circuitry and associated leads that may be employed in the system of FIG. 1 enabling selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include acceleration, oxygen saturation, or spatial sensors.

Figure 3:
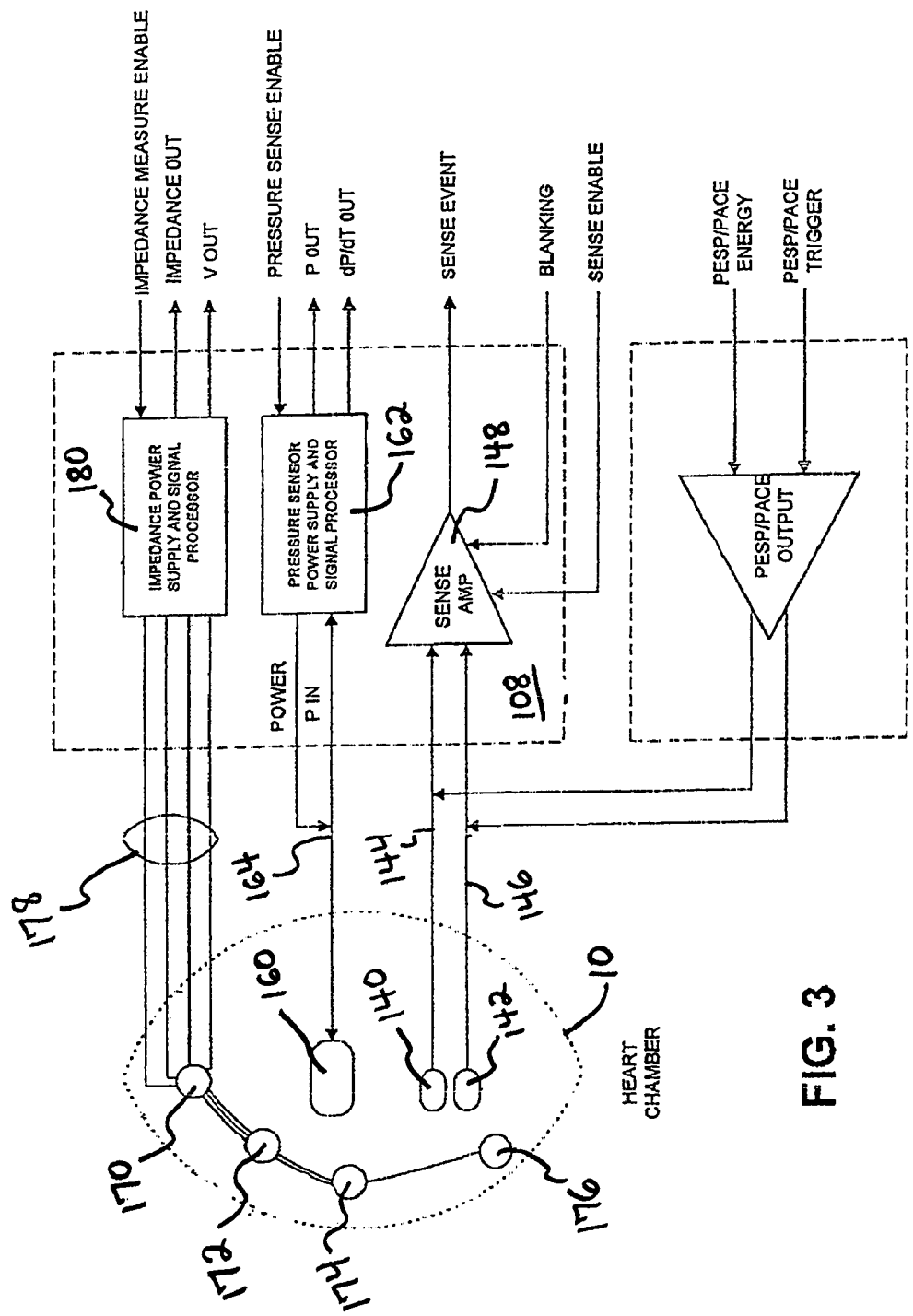
FIG. 3 is a simplified block diagram of a single monitoring and pacing channel for acquiring pressure, impedance and cardiac EGM signals employed in monitoring cardiac functioning and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac electrogram (EGM) recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that my be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256 Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as estimated pulmonary artery diastolic pressure (ePAD), rate of pressure change (dP/dt), etc.

Figure 4:
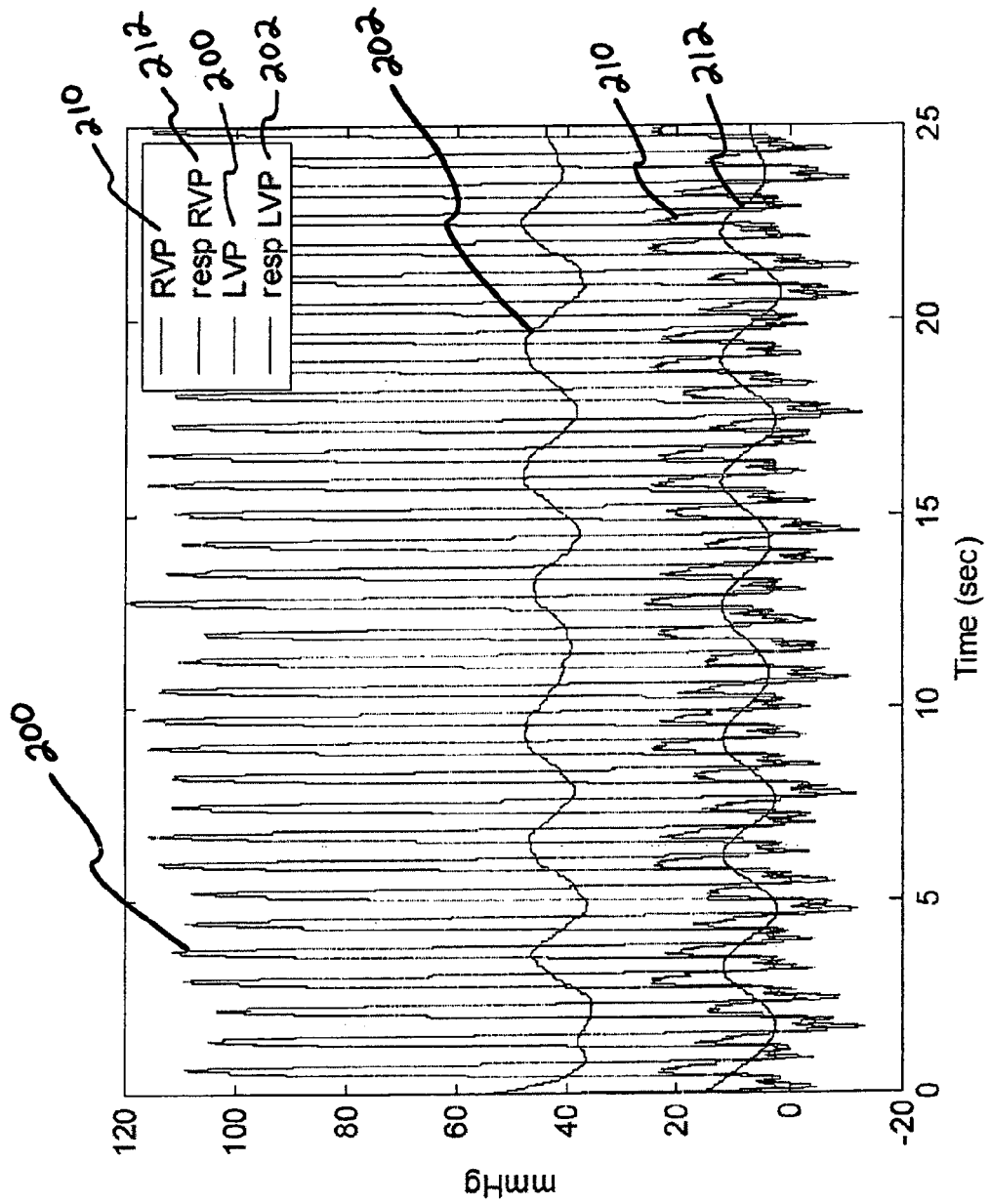
FIG. 4 is a plot of right and left ventricular pressures (RVP and LVP) during a respiration cycle of a patient, as well as respiration waveforms derived therefrom.

FIG. 4 is a plot of right ventricular pressure (RVP) 210 and left ventricular pressure (LVP) 200 acquired during respiration in a patient. RVP and LVP signals 210, 200 may be collected via pressure sensors as part of a medical lead system, for example, as described above. Sample rates for acquiring RVP 210 and LVP 200 may be as high as 256 Hz or higher, for example. Storage of RVP and LVP signals may be by any suitable memory means known in the art.

FIG. 4 also shows respiration waveforms derived from the RVP and LVP signals, 210, 200. For example, Resp-RVP 212 and Resp-LVP 202 are shown superimposed on RVP 210 and LVP 200 in FIG. 4. They may be derived by passing the RVP and LVP signals 210, 200, respectively, through a low-pass filter (such that higher frequency components may be filtered out or removed) according to certain embodiments of the invention.

Figure 5:
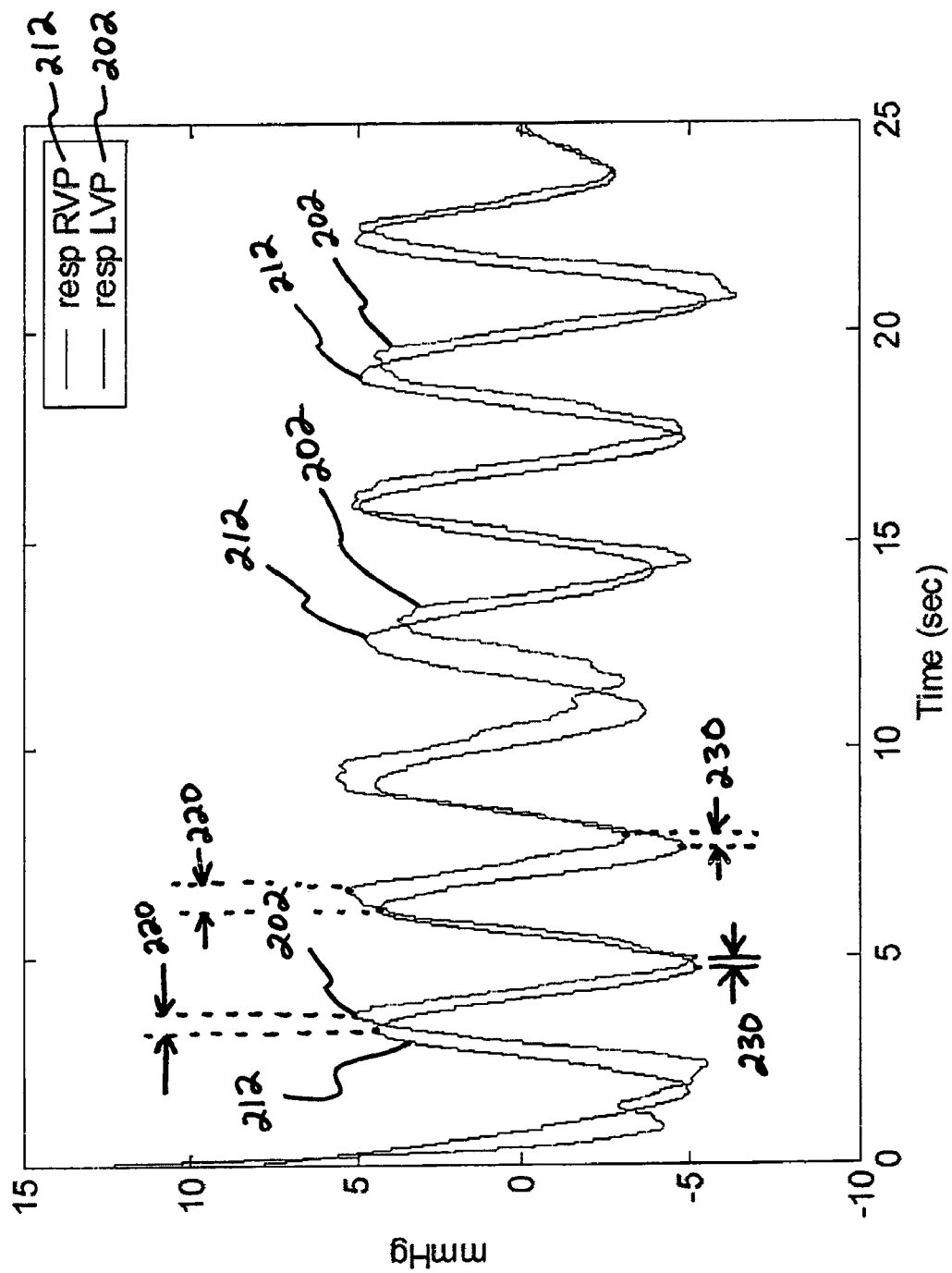
FIG. 5 is a plot showing the phase difference between the right and left respiration waveforms derived in FIG. 4.

FIG. 5 shows the derived Resp-RVP 212 and Resp-LVP 202 signals superimposed upon each other to illustrate the relative phase difference between the two waveforms. This phase difference illustrates an aspect of the respiration effect, namely, that the respiration effect tends to be observed earlier in the right ventricle than in the left ventricle, as shown by the timing offset between respiratory waveforms 212 and 202 in FIG. 5. The phase difference tends to be greater at the peak of inspiration than at the peak of expiration.

In certain embodiments of the invention, the phase difference between the derived respiratory waveforms 212, 202 may be quantified, as shown in FIG. 5. For example, the phase difference between waveforms 212 and 202 at a peak of the respiration waveforms (e.g., expiration) is indicated at reference 220. Similarly, the phase difference between waveforms 212 and 202 at the negative peak of the respective waveforms (e.g., inspiration) is indicated at reference 230. As shown, the magnitude of the phase differences 220, 230 may vary over time, i.e. from respiratory cycle to respiratory cycle.

Figure 6:
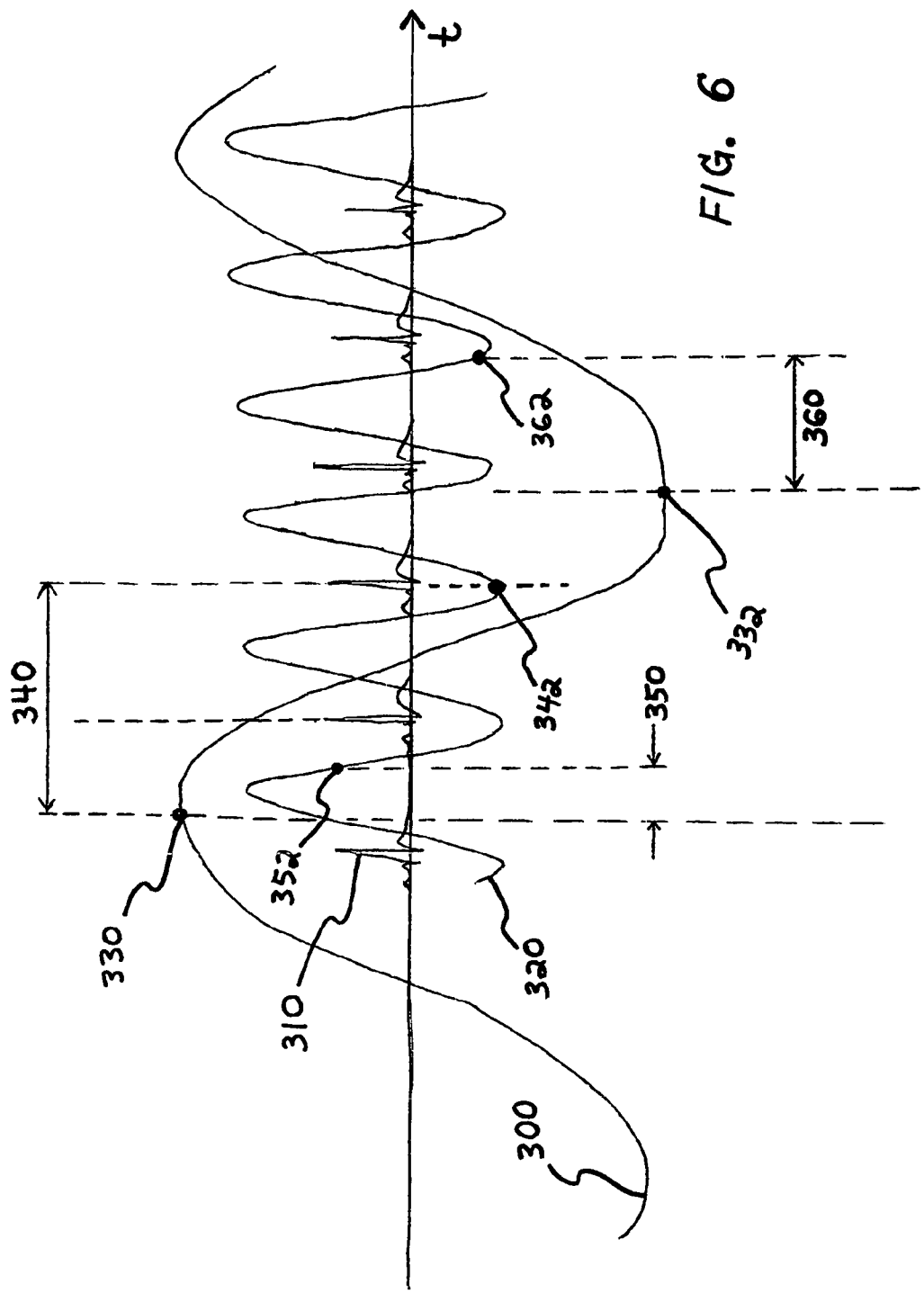
FIG. 6 is a timing plot illustrating alternate methods of setting a timing reference point for data collection based on respiratory cycles in accordance with certain embodiments of the invention.

FIG. 6 is a plot of a respiratory cycle 300 which illustrates a method of sampling patient data that coordinates the timing of the samples to consistently occur at or near the same portion of the respiratory cycle each time a sample is taken. This method may be used to time the collection of hemodynamic data, including hemodynamic pressure data, as well as other forms of monitored patient data, such as impedance (e.g., transthoracic impedance), cardiac electrogram (EGM) signals (e.g., rate and amplitude information), activity signals, and posture signals, for example without limitation. It should be noted that respiratory cycle 300 in FIG. 6 may comprise either the above-described respiration waveforms (i.e., Resp-RVP 212 and Resp-LVP 202), or a combination of the two signals according to certain embodiments of the invention.

Another aspect of the invention enables respiration-gated data sampling.

Fluctuations in measured data due to the respiratory effect may be minimized by sampling data at a recurring point in the respiration cycle. The number of samples needed to obtain a stable average, for example, may be reduced using this method. Data collection for edema monitoring, for example, may comprise measuring the impedance value during the second or third cardiac cycle after a respiration peak (e.g., the peak during inspiration), thereby causing collection of data during approximately the same part of the respiratory cycle for each value sampled. This technique can be expanded to many other data collection schemes employed by a variety of medical device systems and monitoring devices.

Respiratory cycle 300 is shown in FIG. 6 with an ECG signal 310 and a sample data parameter signal 320 (e.g., a hemodynamic pressure signal) superimposed to show the timing relationships between the signals. The positive peak 330 of respiratory cycle 300 is shown as the maximum value of respiratory cycle 300, and the negative peak 332 of respiratory cycle 300 is indicated at the most negative portion of respiratory cycle 300. Peak 330 may correspond to the end of the expiration phase of respiratory cycle 300, while negative peak 332 may correspond to the end of the inspiration phase of respiratory cycle 300. Peak 330 and negative peak 332 may, for example, be used to define timing reference points from which the timing of data collection may be based.

For example, in one data collection scheme, sample parameter 320 may be sampled a predetermined number of cardiac cycles after a timing reference point. This data collection scheme is illustrated by interval 340, which shows data parameter 320 being sampled to obtain data sample 342, corresponding to a time interval 340 defined by the occurrence of a second cardiac event occurring in ECG signal 310 after the occurrence of the timing reference point, in this case peak 330. Of course, as would be apparent to one of ordinary skill in the art, a different point could be chosen for the timing reference point, and a different number of cardiac events may have been chosen to form the basis for interval 340, for example.

Other data collection schemes may be derived in a similar manner. For example, an interval 350 following a timing reference point (such as peak 330 in respiratory signal 300) may be defined as comprising a predetermined number of data sample intervals occurring during interval 350. Sample point 352 corresponds to a sample of data parameter signal 320 obtained using this data collection scheme, for example. A similar data collection scheme is indicated by interval 360 in FIG. 6. In this example, data point 362 is a sample of data parameter 320 obtained by sampling at an interval 360 defined in terms of units of time, e.g., a predetermined number of milliseconds after a timing reference point, in this example, after negative peak 332. It should also be noted that timing reference points other than peak 330 and negative peak 332 may be chosen, and would fall within the scope of the claimed invention.

It should be further noted that, while the respiratory cycle includes two relatively distinct "phases," i.e., the inspiration phase and the expiration phase, the term "phase" may also be used in certain contexts to describe a point or a portion of the respiratory waveform signals. For example, a zero crossing of the respiratory waveform between the end of the inspiration phase and the end of the expiration phase may define a timing reference point according to an embodiment of the invention. In that context, a data collection scheme that samples a parameter waveform during that same "phase" of the respiratory cycle would be understood as described above.

Figure 7:
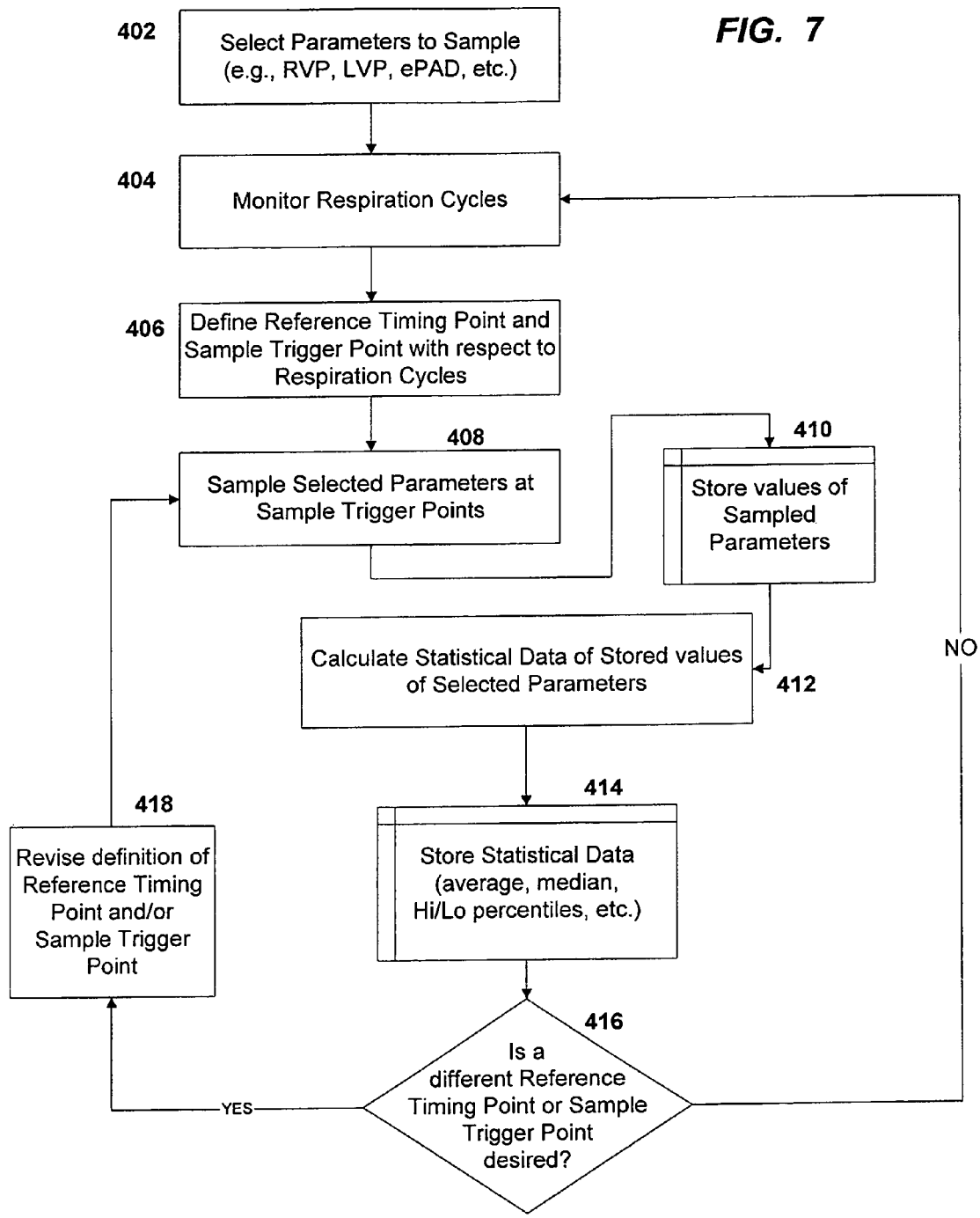
FIG. 7 is a flow chart describing methods of collecting data in accordance with embodiments of the invention wherein the timing of data collection is based on a patient's respiratory cycle.

FIG. 7 is a flow chart that describes a method of collecting data wherein the timing of data collection is based on a patient's respiratory cycle. Step 402 in FIG. 7 includes selecting a data parameter of interest to sample. For example, hemodynamic pressure parameters such as RVP, LVP, and ePAD (which may be derived from RVP, for example), may be chosen as data parameters of interest according to certain embodiments of the invention. Other parameters, including impedance, temperature, oxygen, and activity, for example without limitation, may also be chosen as data parameters of interest in certain embodiments. Step 404 in FIG. 7 comprises monitoring respiration cycles of a patient. As noted above with reference to FIGS. 4 and 5, respiratory cycles may be derived from other signals, such as from right and left ventricular pressure signals, for example. Step 406 comprises defining a timing reference point and a sample trigger point with reference to the monitored respiration cycles from which to time the sampling of the selected data parameters from step 402. Timing reference points may be chosen, for convenience, to be the relative peak values that occur during the respiratory cycle, the relative peaks being either relative maximum or relative minimum values, according to some embodiments. Step 408 in FIG. 7 comprises sampling the selected data parameters at the sample trigger points defined in step 406. In certain embodiments, the sampling of data parameters at sample trigger points need not occur every respiratory cycle, but may occur spaced apart by a number of respiratory cycles that may be periodic or random, for example. In still further embodiments, the number of respiratory cycles between sample trigger points (and hence, between data samples) may be varied (e.g., increased) in response to changes in a data parameter, such as heart rate, respiration rate, and blood pressure, for example without limitation. This may, for example, provide additional data resolution at periods of time that may be of particular interest.

In certain embodiments of the invention, the sampled parameters may be stored, as shown by step 410 in FIG. 7. Sample parameter values may be stored in a variety of memory means, including RAM, ROM, and various forms of memory buffers, for example. Step 412 may comprise calculating statistical information from the stored parameter values from step 410. For example, step 412 may include calculating an average value, or a median value, or certain percentile values over given periods of time, for example. Step 412 may further include a predetermined sampling interval over which statistical calculations are periodically performed on the data stored in step 410. For example, a sampling interval of six minutes may be used to periodically perform statistical calculations on data stored in a memory buffer, for example, and the memory buffer cleared out (erased) after each such statistical calculation. Step 414 may include storing the statistical data calculated in step 412 for later display and/or analysis.

In certain embodiments of the invention, it may be desirable to change the timing reference point for data collection, possibly based on information acquired during data collection, or due to operator (e.g., physician) preference, for example. If a revision of the timing reference point is desired, step 418 allows for making such a change. It should be noted that in certain embodiments of the invention, it may be desirable to have multiple timing reference points defined within a given respiratory cycle. For example, it may be desirable to collect two or more sets of data, one occurring at points in time referenced to the end of the inspiration phase, and the other set of data points collected at points in time referenced from the end of the expiration phase, in one possible example. This may involve defining two or more reference timing points. Alternately, a reference timing offset (or offsets) may be employed to collect multiple sets of data, the offsets defined with reference to a single timing reference point, for example. Other minor modifications to the steps described in FIG. 7 may become apparent to those of ordinary skill in the art with the benefit of these teachings and are considered to fall within the scope of the claimed invention.

Another aspect of the invention also enables respiration-gated therapy delivery.

Respiration patterns and phases may play a role in "synchronization" of the ventricular contraction. For example, cardiac pacing parameters such as atrio-ventricular (AV) delay and inter-ventricular (V-V) delay, may be varied to affect the synchronization of ventricular contractions. V-V delay may comprise the time interval from the occurrence of a depolarization event in one ventricular chamber to the programmed delivery of a pacing stimulus in the other ventricular chamber. The optimal V-V delay may be adjusted, for example, to be different during inspiration than during expiration to achieve the desired synchronization of ventricular contraction. This will be described in more detail below. Further, the respiration effect may be more pronounced in patients with congestive heart failure (CHF). For example, a preliminary analysis shows a statistically significant difference in "degree" of synchronization between RV and LV contractions which may be correlated with the respiration effect in patients with CHF.

Figure 8:
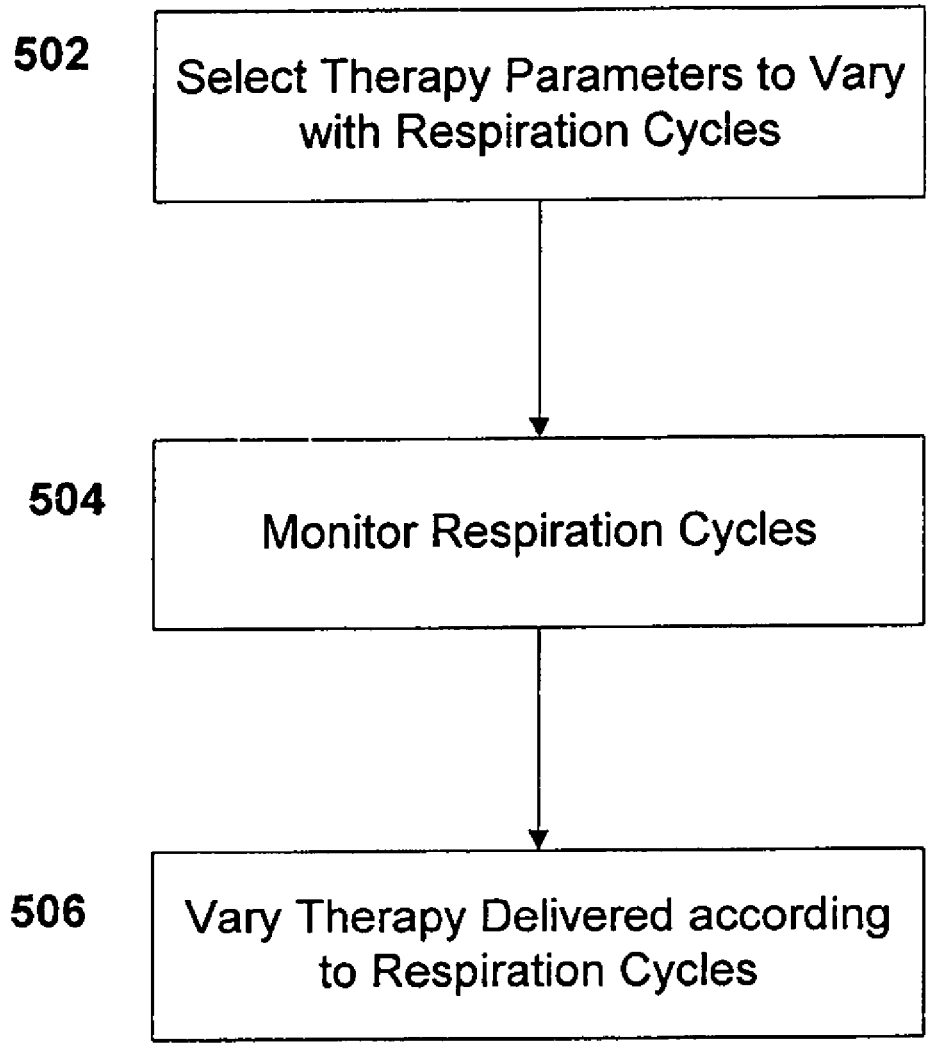
FIG. 8 is a flow chart describing methods of delivering therapy to a patient using information from a patient's respiratory cycle in accordance with embodiments of the invention.

A method of providing respiration-influenced therapy delivery is described in FIG. 8. More specifically, FIG. 8 is a flow chart describing a method of delivering therapy to a patient using information from a patient's respiratory cycle to vary the therapy parameters.

Step 502 in FIG. 8 comprises selecting therapy parameters to vary with respiration cycles. Therapy parameters may include, for example, cardiac pacing parameters, drug delivery parameters, or any other therapy parameters selected by an operator. In certain embodiments, for example, cardiac pacing parameters such as AV delay and/or inter-ventricular delay (V-V delay) may be selected as the therapy parameters to vary according to a patient's respiratory cycle. Step 504 in FIG. 8 includes monitoring the respiration cycles of a patient. This may be done substantially as described in Step 404 with reference to FIG. 7 above, for example.

Step 506 includes varying the therapy delivered according to the respiratory cycles of a patient. As noted previously, cardiac pacing parameters such as AV delay and V-V delay may be varied according to the respiratory cycle to improve synchronization of ventricular contractions, according to certain embodiments of the invention.

Figure 9A:
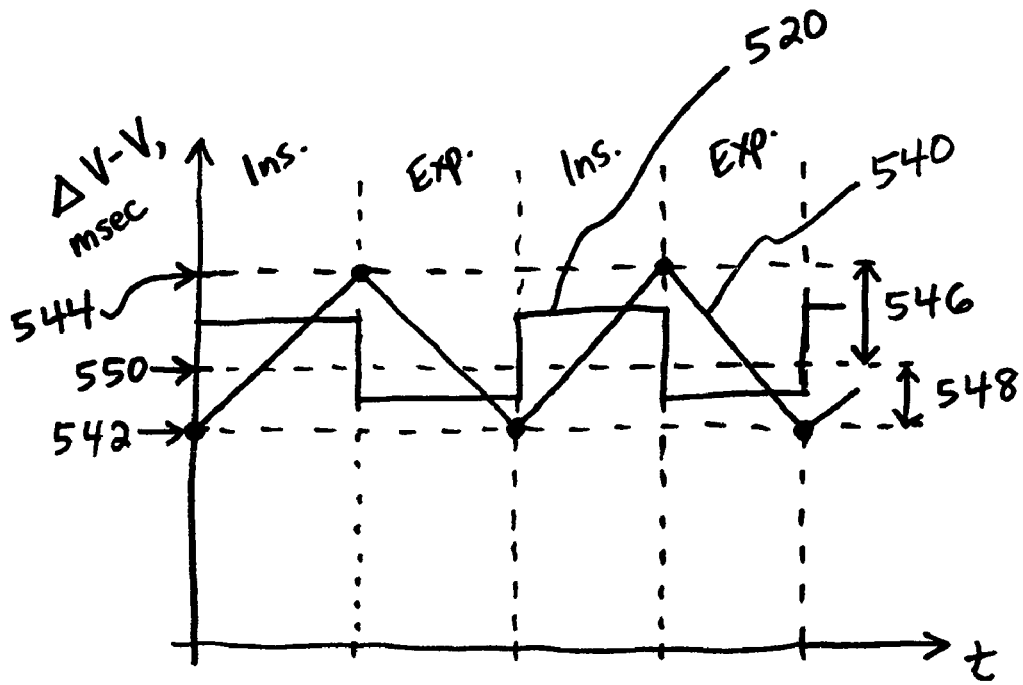
FIGS. 9(a) and 9(b) are timing plots illustrating alternate methods of varying therapy delivery to a patient based on respiratory cycle information.
Figure 9B:
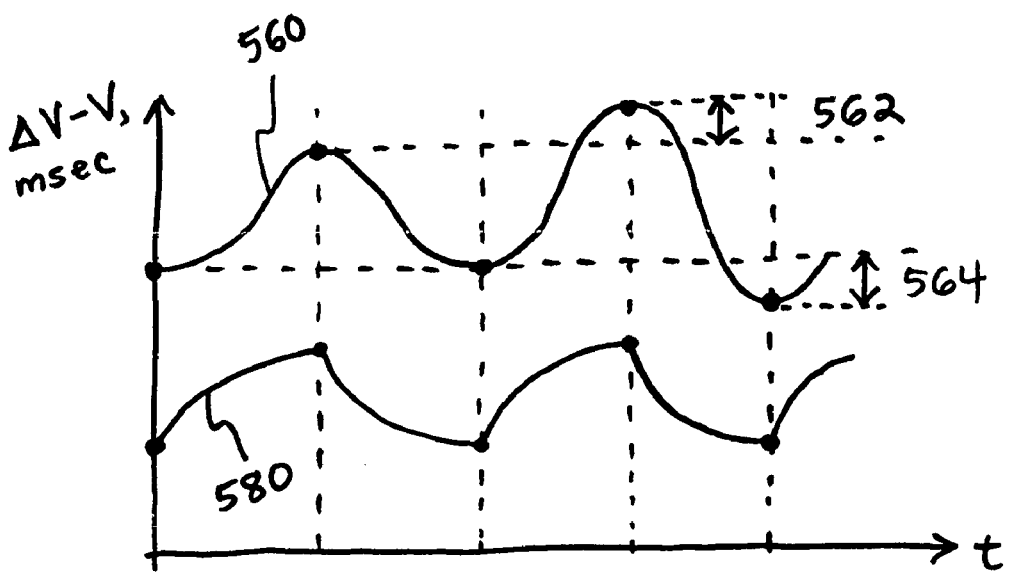

FIGS. 9(a) and 9(b) illustrate how a particular therapy parameter, in this example, V-V delay, may be varied throughout a respiratory cycle of a patient in order to improve the therapy delivered to the patient.

FIG. 9(a) provides two examples of ways in which a therapy parameter (e.g., V-V delay) may be varied throughout a respiratory cycle in order to improve the therapy delivered (e.g., improve synchronization of ventricular contractions). Waveform 520 in FIG. 9(a), for example, is an example of alternating between one value for the therapy parameter during the inspiration phase of the respiratory cycle, and a second value of the therapy parameter to deliver during the expiration phase of the respiratory cycle. In the example shown, the V-V delay (e.g., the timing difference between a paced stimulus in the right ventricle and a paced stimulus in the left ventricle), is varied between one value used during the inspiration phase, and a second value (e.g., a shorter V-V delay interval in this example) during the expiration phase. The shape (or phase) of waveform 520 could alternately be modified so that the V-V delay is greater during the expiration phase than during the inspiration phase, for example.

Also shown in FIG. 9(a) is waveform 540, which is another method of varying the therapy parameter delivered according to the respiration cycles of a patient. For example, waveform 540 varies (e.g., increases) linearly from a first (e.g., a minimum) value 542 to a second (e.g., maximum) value 544 during the inspiration phase, then varies (e.g., decreases) linearly from a value 544 to a value 542 during the expiration phase. The linear variability described by waveform 540 could alternately be described using positive and negative deviations 546, 548 from a central or middle value 550, according to certain embodiments of the invention. Other forms of linearly varying a therapy parameter during a respiratory cycle may be devised by one of ordinary skill in the art with the benefit of these teachings, and would be deemed to fall within the scope of the invention as claimed.

FIG. 9(b) shows additional methods by which a therapy parameter may be varied according to the respiratory cycle of a patient. Waveform 560 in FIG. 9(b), for example, shows a therapy parameter (e.g., V-V delay) being varied according to a substantially sinusoidal waveform shape that has a positive peak at or near the end of the inspiration phase, and a minimum or negative peak at or near the end of the expiration phase. Additionally, waveform 560 illustrates that the amount of variability of the therapy parameter may be varied from respiratory cycle to respiratory cycle according to certain embodiments of the invention. For example, the peak positive value of waveform 560 and the peak negative or minimum value of waveform 560 are shown to have increased or decreased by the amounts indicated by reference numerals 562 and 564, respectively. Also shown in FIG. 9(b) is waveform 580, yet another example of a method by which the therapy parameter may be varied with respiratory cycles of a patient. Waveform 580 is a "decay"-type waveform which shows the therapy parameter increasing at a decreasing rate during the inspiration phase, and subsequently decreasing at a decreasing rate during the expiration phase. Waveform 580 may, for example, be mathematically described using an exponential decay function, according to some embodiments of the invention. It should be noted that the examples provided in FIGS. 9(a) and 9(b) are exemplary only and may be modified further by one of ordinary skill in the art with the benefit of these teachings. Such modifications would be considered to fall within the scope of the claimed invention.

Thus, embodiments of a METHOD OF OPTIMIZING DATA COLLECTION AND THERAPY DELIVERY BASED ON RESPIRATION are disclosed. One skilled in the art will appreciate that the invention can be practiced with embodiments other than those disclosed. The disclosed embodiments are presented for purposes of illustration and not limitation, and the invention is limited only by the claims that follow.

The invention claimed is:

1. A computer-readable medium programmed with instructions for performing a method of collecting hemodynamic data in an implantable medical device, the medium comprising instructions for causing a programmable processor to:
    monitor respiratory cycles of a patient, including determining when an inspiration phase is occurring and when an expiration phase is occurring;
    identify at least one timing reference point of a respiratory cycle;
    collect a set of hemodynamic data from the patient at intervals based on the at least one timing reference point of a respiratory cycle such that all data in the set were obtained during approximately the same portion of the respiratory cycle; and
    collect multiple sets of hemodynamic data using multiple timing reference points.

2. A medium according to claim 1 further comprising instruction to determine the inspiration and expiration phases of the respiratory cycle by low-pass filtering a hemodynamic pressure signal of the patient.

3. A medium according to claim 2 wherein the hemodynamic pressure parameter is right ventricular pressure.

4. A medium according to claim 1 wherein the first and second sets of therapy parameters include cardiac pacing parameters.

5. A medium according to claim 4 wherein the cardiac pacing parameters include at least an interventricular paced timing delay, comprising a time interval from the occurrence of a depolarization event in one ventricular chamber to the programmed delivery of a pacing stimulus in the other ventricular chamber.

6. A medium according to claim 5 wherein the interventricular paced timing delay of the first set of therapy parameters is different from the interventricular timing delay of the second set of therapy parameters.

7. A medium according to claim 6 wherein the interventricular timing delay of the first set of therapy parameters is greater than the interventricular timing delay of the second set of therapy parameters.

8. A medium according to claim 4 wherein the cardiac pacing parameters include at least an atrio-ventricular (AV) delay.

9. A medium according to claim 1 wherein the at least one timing reference point of a respiratory cycle includes a relative peak value that occurs during the respiratory cycle.

10. A medium according to claim 1 further comprising instructions to sample the hemodynamic data at most once per respiratory cycle to collect the set of hemodynamic data.

11. A medium according to claim 10 further comprising instructions to vary the number of respiratory cycles between successive hemodynamic data samples.

12. A medium according to claim 11 further comprising instructions to vary the number of respiratory cycles between successive hemodynamic data samples in response to changes in respiration rate.

13. A computer-readable medium programmed with instructions for performing a method of collecting hemodynamic data in an implantable medical device, the medium comprising instructions for causing a programmable processor to:
    monitor respiratory cycles of a patient, including determining when an inspiration phase is occurring and when an expiration phase is occurring;
    identify at least one timing reference point of a respiratory cycle;
    collect a set of hemodynamic data from the patient at intervals based on the at least one timing reference point of a respiratory cycle such that all data in the set were obtained during approximately the same portion of the respiratory cycle; and
    collect multiple sets of hemodynamic data using a single timing reference point and at least one reference offset.

14. A medical device system comprising:
    means for monitoring respiratory cycles of a patient, including determining when an inspiration phase is occurring and when an expiration phase is occurring;
    means for identifying at least one timing reference point of a respiratory cycle;
    means for collecting a set of hemodynamic data from the patient at intervals based on the at least one timing reference point of a respiratory cycle such that all data in the set were obtained during approximately the same portion of the respiratory cycle; and
    means for collecting multiple sets of hemodynamic data using multiple timing reference points.

15. A system according to claim 14 further comprising:
    means for delivering a first set of therapy parameters during the inspiration phase; and
    means for delivering a second set of therapy parameters different from the first set during expiration phase.

16. A system according to claim 15 wherein the first and second set of therapy parameters includes cardiac pacing parameters including at least an interventricular paced timing delay (V-V delay), the V-V delay comprising a time interval from the occurrence of a depolarization event in one ventricular chamber to the programmed delivery of a pacing stimulus in the other ventricular chamber.

17. A system according to claim 14 further comprising means for delivering therapy parameters that vary substantially linearly as a function of the phase of the patient's respiratory cycle.

18. A system according to claim 14 further comprising means for delivering therapy parameters that vary by different amounts between respiratory cycles.

19. A system according to claim 14 further comprising instruction to determine the inspiration and expiration phases of the respiratory cycle by low-pass filtering a hemodynamic pressure signal of the patient.

20. A system according to claim 19 wherein the hemodynamic pressure parameter is right ventricular pressure.

21. A system according to claim 14 wherein the first and second sets of therapy parameters include cardiac pacing parameters.

22. A system according to claim 21 wherein the cardiac pacing parameters include at least an interventricular paced timing delay, comprising a time interval from the occurrence of a depolarization event in one ventricular chamber to the programmed delivery of a pacing stimulus in the other ventricular chamber.

23. A system according to claim 22 wherein the interventricular paced timing delay of the first set of therapy parameters is different from the interventricular timing delay of the second set of therapy parameters.

24. A system according to claim 23 wherein the interventricular timing delay of the first set of therapy parameters is greater than the interventricular timing delay of the second set of therapy parameters.

25. A system according to claim 21 wherein the cardiac pacing parameters include at least an atrio-ventricular (AV) delay.

26. A medical device system comprising:
    means for monitoring respiratory cycles of a patient, including determining when an inspiration phase is occurring and when an expiration phase is occurring;
    means for identifying at least one timing reference point of a respiratory cycle;
    means for collecting a set of hemodynamic data from the patient at intervals based on the at least one timing reference point of a respiratory cycle such that all data in the set were obtained during approximately the same portion of the respiratory cycle; and
    means for collecting multiple sets of hemodynamic data using a single timing reference point and at least one reference offset.

* * * * *

UNITED STATES PATENT AND TRADEMARK OFFICE
CERTIFICATE OF CORRECTION

| | | |
|---|---|---|
| PATENT NO. | : 7,623,917 B2 | Page 1 of 1 |
| APPLICATION NO. | : 11/322761 | |
| DATED | : November 24, 2009 | |
| INVENTOR(S) | : Cho et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 910 days.

Signed and Sealed this

Twenty-sixth Day of October, 2010

David J. Kappos
*Director of the United States Patent and Trademark Office*